United States Patent [19]

Parris et al.

[11] Patent Number: 4,950,690
[45] Date of Patent: Aug. 21, 1990

[54] PROCESS FOR THE ANIMATION OF ALCOHOLS USING ACTIVATED PHOSPHORUS-CONTAINING CATALYSTS

[75] Inventors: Gene E. Parris, Revere; Ronald Pierantozzi, Orefield, both of Pa.

[73] Assignee: Air Products and Chemicals, Inc., Allentown, Pa.

[21] Appl. No.: 277,081

[22] Filed: Nov. 28, 1988

[51] Int. Cl.$^5$ .................. C07B 211/04; C07C 209/16
[52] U.S. Cl. ..................................... 546/184; 564/401; 564/447; 564/479
[58] Field of Search .................. 564/479, 401, 447; 546/184

[56] References Cited

U.S. PATENT DOCUMENTS

| | | | |
|---|---|---|---|
| 3,265,012 | 5/1980 | Parker et al. | 564/479 |
| 4,049,657 | 9/1977 | Brennan et al. | 260/268 |
| 4,082,805 | 4/1978 | Kaeding | 260/585 |
| 4,103,087 | 7/1978 | Brennan, III | 564/479 |
| 4,117,227 | 9/1978 | Brennan | 544/170 |
| 4,205,012 | 5/1980 | Parker et. al. | 564/479 |
| 4,448,997 | 5/1984 | Brennan, IV | 564/479 |
| 4,501,889 | 2/1985 | Wells et al. | 544/106 |

FOREIGN PATENT DOCUMENTS 2147896  5/1985  United Kingdom ................ 564/479

Primary Examiner—Richard L. Raymond
Assistant Examiner—Mark W. Russell
Attorney, Agent, or Firm—Keith D. Gourley; James C. Simmons; William F. Marsh

[57] ABSTRACT

The present invention is a process for selectively aminating alcohols wherein a mixture of an amine and a primary or secondary alcohol or diol is contacted with a catalytically effective amount of a phosphorus-containing catalyst which has been impregnated or titrated with a metal cation salt composition represented by the formula:

$$M_a{}^{m+}X_b{}^{n-}$$

wherein $M^{m+}$ is a cation selected from Group Ia and IIa of the Periodic Table of the elements having a valence m, $X^{n-}$ is an organic or inorganic anionic species having a valence n, and a and b are integers such that the ratio of a to b provides a neutral salt. A typical reaction includes the amination of ethanol with piperidine to form N-ethylpiperidine.

17 Claims, No Drawings

PROCESS FOR THE ANIMATION OF ALCOHOLS USING ACTIVATED PHOSPHORUS-CONTAINING CATALYSTS

TECHNICAL FIELD OF THE INVENTION

The present invention relates to a process for the catalytic amination of 1° and 2° alcohols and diols wherein an alcohol and an amine are reacted in the presence of a phosphorus-containing catalyst which has been activated by base treatment with an alkali or alkaline earth metal cation salt composition.

BACKGROUND OF THE INVENTION

Current processes for the amination of alcohols and diols typically use heterogeneous catalysts comprising supported transition metals with known hydrogenation/dehydrogenation activity and/or acidic compositions, in particular, zeolites, mixed oxides and metal phosphates. Unfortunately, such catalyst systems present numerous process limitations. For example, catalysts containing transition metals typically yield by-product amines and olefins which may cause catalyst deactivation and often produce undesireable aldehyde-type by-products. Acidic catalysts are usually non-selective in alcohol amination reactions yielding the corresponding ether, unsaturated hydrocarbon, polymeric products and scrambled amines as by-products formed via transalkylation and disproportionation reactions.

Acidic catalysts also tend to dehydrate alcohols to form olefin or ether by-products thereby reducing the yield of the desired N-alkylation product. Alkene formation can be reduced somewhat by operating the process at lower temperatures. Unfortunately, lower reaction temperatures necessitate use of a lower ratio of amine/alcohol in order to achieve sufficiently high amine conversion Additionally, both acidic and dehydrogenation type catalysts inherently require some recycle of unconverted reactants.

Several processes have been developed using acidic metal phosphate catalysts. More particularly. phosphates of boron, aluminum and trivalent iron have been proposed for use in intramolecular cyclic dehydration reactions and other condensation reactions involving amine compounds. Examples of such reactions are found in U.S. Pat. No. 4,117,227 which discloses conversion of an N-substituted diethanolamine to the corresponding N-substituted morpholine. Additionally, U.S. Pat. No. 4,049,657 discloses the reaction of piperidine with ethanolamine over metal phosphate catalysts to produce N-aminoethyl piperidine.

U.S. Pat. No. 4,082,805, relates to a process for the production of aliphatic amines wherein a $C_1$ to $C_5$ alcohol or ether is reacted with ammonia in the presence of a crystalline aluminosilicate catalyst having the structure of ZSM-5, ZSM-11 or ZSM-21. Preferred catalysts have a high silica to alumina ratio typically greater than 5 and preferably greater than 30. The reaction is effected at a temperature between 300° C. and about 500° C. and a pressure between atmospheric and 1000 psig. The relative feed rates, expressed in grams per hour of alcohol or ether to ammonia, typically range from 1:1 to about 5:1.

U.S. Pat. No. 4,501,889, assigned to Air Products and Chemicals, Inc., discloses a process for preparing morpholine compounds by reacting 2-(2-aminoethoxy)ethanol in the presence of an effective amount of catalyst selected from the group consisting of the pyrophosphate, monohydrogen phosphate and the dihydrogen phosphate of strontium, copper, magnesium, calcium, barium, zinc, aluminum, lanthanum, cobalt, nickel, cerium and neodymium and mixtures thereof. Preferred catalysts are the soluble metal salts of strong acids such as metal nitrates in substantially stoichiometric proportion to the phosphate.

SUMMARY OF THE INVENTION

This invention pertains to a process for selectively producing N-alkylated aromatic and aliphatic amines wherein a 1° or 2° alcohol or diol and an amine are reacted in the presence of a phosphorus-containing catalyst activated by base treatment. More particularly, the phosphorus-containing catalyst is activated by impregnation or titration with an alkali metal or alkaline earth metal cation salt. The activated catalyst employed in the process may optionally be used with suitable supports known in the art.

Phosphorus-containing catalysts suitable for activation with an alkali or alkaline earth metal cation salt include phosphoric acid compounds and their anhydrides, phosphorous acid compounds and their anhydrides, alkyl or aryl phosphate esters, alkyl or aryl phosphite esters and alkyl or aryl substituted phosphorous acids and phosphoric acids. These phosphorus-containing catalysts are then activated by impregnating or titrating the catalyst with a metal cation salt represented by the formula:

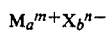

$$M_a{}^{m+}X_b{}^{n-}$$

wherein $M^{m+}$ is a cation selected from Group Ia or IIa of the Periodic Table of the elements having a valence m, $X^{n-}$ is an organic or inorganic anionic species having a valence n, and a and b are integers such that the ratio of a to b provides a neutral salt. Representative of suitable cation salts are the hydroxides, alkoxides and nitrates of lithium, sodium and cesium, to name a few.

The process can be run effectively as a vapor phase reaction at temperatures ranging from about 150° C. to about 500° C. and pressures ranging from about 1 to 100 atmospheres as well as a liquid phase reaction at temperatures ranging from about 100° C. to about 400° C. A preferred embodiment of the process relates to the amination of ethanol with piperidine wherein the reaction catalyst employed is $H_3PO_4$ supported on $Al_2O_3$ which is activated by base treatment via impregnation with sodium hydroxide.

DETAILED DESCRIPTION OF THE INVENTION

Early processes for the production of N-alkylated amInes wherein an amine is reacted with an alcohol or diol in the presence of a heterogeneous acidic catalyst typically resulted in poor reaction rates and low selectivity toward the desired N-alkylated product. Typical catalysts often produced unexceptable amounts of undesirable by-products including the corresponding ether, unsaturated hydrocarbons and scrambled amines.

The improved process of this invention substantially reduces the formation of such undesirable by-products while exhibiting high selectivity toward the desired N-alkylated product. The increased selectivity is realized without an adverse effect on conversion of the amine to the desired product. These results represent a departure from typical heterogeneous catalysts disclosed in the prior art wherein increased selectivity is typically obtained at the expense of reactant conversion.

The improvement to the basic process for the catalytic amination of 1° and 2° alcohols and diols resides in the use of phosphorus-containing catalysts activated by base treatment with a Group Ia or IIa metal cation salt composition. Processes for the amination of alcohols and diols utilizing phosphorus-containing catalysts known in the art can be substantially improved by base treatment with an effective amount of a Group Ia or IIa cation metal salt sufficient to render basic the acidic sites on the catalyst surface. Activation of phosphorus-containing materials by cation salt treatment is conveniently effected by impregnating or titrating the catalyst with a solution of cation metal salt having a pH in the range of about 7 to 11.5 as will be described herein in greater detail.

Preferred phosphorus-containing catalysts for practicing the claimed process include phosphoric acid compounds and their anhydrides, phosphorous acid compounds and their anhydrides, alkyl or aryl phosphate esters, alkyl or aryl phosphite esters and alkyl or aryl substituted phosphorous acids and phosphoric acids. Additionally, any commercially available mono-, di-, or tri-alkyl phosphate or phosphite ester can be employed as the catalyst in the process. Moreover, bis(phosphates) and secondary phosphate esters such as those disclosed in U.S. Pat. Nos. 3,869,526 and 3,869,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted group.

Suitable alkyl or aryl substituted phosphorus acids which may be employed as catalysts in this process include alkyl phosphonic acids, aryl phosphonic acids and aryl phosphinic acids. Preferably, such acids include alkyl or aryl groups and have from 1 to about 8 carbon atoms in each alkyl group and about 6 to 20 carbon atoms in each aryl group.

The above-mentioned phosphorus-containing catalysts are not intended to be exhaustive of those which may be activated by base treatment and utilized in the process of the present invention. Additional catalysts suitable for practicing the claimed process are boron phosphate, aluminum phosphate, ferric phosphate, titanium phosphate, zirconium phosphate and lanthanum phosphate.

The phosphorus-containing catalysts described herein are activated toward selective amination of 1° and 2° alcohols and diols by base treatment wherein such catalysts are impregnated or titrated with a solution of a metal cation salt compound represented by the formula

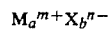

wherein $M^{m+}$ is a cation selected from Group Ia or IIa if the Periodic Table of the elements having a valence m, $X^{n-}$ is an organic or inorganic anionic species having a valence n, and a and b are integers such that the ratio of a to b provides a neutral salt. Representative of suitable anionic species are the hydroxides, alkoxides and nitrates of lithium, potassium, calcium, sodium and cesium, to name a few.

Base treatment of phosphorus-containing catalysts can also be effected by impregnation or titration of the catalyst with alkyl compounds of metals selected from Group Ia and IIa of the Periodic Table of the elements. Typical compounds include $C_1$–$C_4$ alkyl metal salts such as methyl lithium, tert-butyl lithium and diethyl magnesium.

The activated phosphorus-containing catalysts of the present process can be prepared by two alternate methods. In the first method, the phosphorus-containing catalyst is impregnated with the metal cation salt compound. Impregnation is usually performed by insipiently wetting the phosphorus-containing catalyst with an amount of metal cation solution equal to the pore volume of the catalyst to be treated. The quantity of metal cation solution utilized is at least one equivalent, or up to an excess of about 20% of the phosphorus content of the catalyst. Selection of the solvent to be employed is not critical to the invention and those solvents known and used in the art for solubilizing metal cation salt compounds can be used.

Alternatively, up to a 10% excess of impregnating solution based upon total catalyst pore volume may be used to ensure that the entirety of catalyst surface pores has been impregnated with a Group Ia or IIa metal cation salt. When larger excesses of impregnating solution are used, the catalyst/solution mixture is dried with stirring to ensure even distribution of the activating cation onto the catalyst surface. The activated catalyst may optionally be subjected to calcination under standard conditions to desorb/decompose residual anionic species from the catalyst which may deactivate the catalyst.

The second method utilizes a titration technique wherein a solution of metal cation salt having a pH between about 7 and 11.5 is prepared. The phosphorus-containing catalyst is added stepwise into the solution to form a slurry and the pH of the slurry is continuously adjusted by titrating additional metal cation salt into the slurry to maintain the pH between about 9 and 11.5. In an equally preferred embodiment, the phosphorus-containing catalyst is added to distilled water having a neutral pH. The solution containing the phosphorus-containing catalyst is then titrated to a final pH of between about 9 and about 11.5. The catalyst is then filtered and dried without washing.

Suitable Group Ia and IIa metal cation salt compounds for practicing this process include calcium hydroxide, calcium nitrate, sodium hydroxide, lithium hydroxide and potassium hydroxide. When using the titration method for preparing activated catalyst, the concentration of the metal cation salt solution should be regulated to avoid raising the pH of the catalyst to an undesirably high level of basicity which could adversely affect catalyst reactivity. Typically a 0.05 to 0.3 molar basic solution is used.

A wide range of aromatic and aliphatic amines are suitable as aminating agents in the disclosed process. Representative of such amines are 1° and 2° aliphatic and aromatic amines. Such 1° and 2° amines may vary broadly in structure and their use in this amination process is limited only by the solubility of the particular amine in the reaction solvent. Preferred aminating agents include methylamine, ethylamine, piperidine, diethylamine, cyclohexylamine and aniline.

Alcohols and diols suitable for practicing this invention include $C_1$–$C_8$ linear and branched acyclic, cyclic and aromatic alcohols including but not limited to methanol, ethanol, isopropanol, ethylene glycol, benzyl alcohol, butanediol and benzenedimethanol. It shall be understood that when alcohols are discussed, the invention also contemplates the use of diols.

The process of this invention may take place in the liquid or gas phase. Temperatures from about 150° to 500° C. and pressures from about 1 to 100 atmospheres are contemplated when employing the catalysts in a gas phase reaction. In contrast, the pressure utilized in carrying out liquid phase reactions is that autogenous pressure which is sufficient to maintain the reaction in essentially the liquid phase although higher pressures may be used. Liquid phase reaction temperatures may range from about 100° to 400° C. When utilizing these temperatures and pressures in liquid phase reactions, the process is allowed to proceed until a desired conversion to product is obtained or the reaction is complete.

Flow rates, expressed as liquid hourly space velocity (LHSV) for a continuous reaction using a fixed bed system in which the base treated phosphorus-containing catalyst is present in bulk form or in conjunction with an inert support, typically range from about 0.1 to 4 hours$^{-1}$ depending upon the particular aminating agent used.

The quantity of base treated phosphorus-containing catalyst used in the process is empirical and can vary widely depending upon the reactivity of the activated catalyst and reactants. An effective amount of activated catalyst is used in the amination process; i.e., an amount which causes a reaction between the alcohol and the amine to yield the desired N-alkylated amine at the temperature and pressure used. Usually, the amount of active catalyst used to provide a catalytic effect in fixed or continuous bed reaction systems ranges from about 0.05 to 10 mole% based upon the amount of aminating agent present in the reaction mixture, and preferably ranges from about 0.5 to 4 mole%. Within these ranges though, the amount of catalyst is empirical and is adjusted depending on the desired product since amine products may be generated in an equilibrium distribution.

Generally, the mole ratio of reactants ranges from about 1:4 to 20:1 amine/alcohol, and preferably ranges from about 1:3 to 10:1 amine/alcohol. The process may be carried out advantageously by regulating the proportion of aminating agent to alcohol such that a stoichiometric excess of aminating agent is used, e.g., from about 1.1:1 to a 20:1 ratio of aminating agent to alcohol which results in formation of predominantly the desired amination product.

The activated phosphorus-containing catalysts of the present invention may be employed in particle or pellet form. Catalyst particle size is not critical to the practice of the claimed process. Catalyst particles are typically formed by breaking up the washed and dried filter cake obtained by following the procedures enumerated in the examples disclosed herein. Catalyst pellets can be formed by casting and extruding methods well known in the art. These activated catalysts may also be deposited on or impregnated into the pores of a porous substrate. The activated phosphorous-containing catalysts may be calcined at a temperature between 250° and 600° C.

The process of the invention can be carried out batch wise or continuously by employing well known batch and continuous processing techniques and conventional processing apparatus. In such continuous reaction processes, the above-described activated phosphorus-containing catalysts may be employed as a feed stream alone or admixed with a reactant feed stream or they may be employed as a fixed bed catalyst in a continuous reactor system.

Generally, suitable fixed bed catalysts comprise the catalyst supported on a reactor packing material such as silica, silica-alumina, alumina, magnesia or diatomaceous earth. Such fixed bed supported catalysts and procedures for their preparation are well known in the art and many are readily available commercially.

Recovery of the desired N-alkylation product from the reaction mixture is accomplished by conventional techniques including but not limited to a fractionation step such as distillation. A particular advantage in practicing this invention relates to the simplified separation and purification steps required to isolate the desired products based upon the high selectivity afforded by these catalysts. For example, the reaction products may be distilled directly or if necessary, filtered prior to distillation to remove solids in the form of amine/catalyst complexes which may have formed during the reaction.

In using catalysts of the present process for amination of 1° and 2° alcohols and diols, substantially the same conditions may be employed as when using known amination catalysts for the particular synthesis For optimum results, however, some adjustment in the temperature, pressure, diluent and/or space velocity may be found beneficial.

The following examples illustrate the nature of the process described herein are not intended to limit the scope of the invention.

Example 1

Preparation of a Phosphate/Alumina Catalyst

This example illustrates preparation of a known phosphate/alumina catalyst. 300g of Catapal alumina was placed in a muffle furnace at 500° C. for 8 hrs. The final dried weight was 214g. To 161g of the calcined alumina was added 0.08L of $H_3PO_4$ solution containing 12.6g $H_3PO_4$ in deionized water. The solid was mixed thoroughly with a mortar and pestle during slow addition of the $H_3PO_4$ which incipiently wetted the alumina. The solid was dried at 110° C. for 4 hours. The material was analyzed to contain 1.98 wt% phosphorus.

Example 2

Preparation of an Activated Phosphate/Alumina Catalyst

This example illustrates preparation of a phosphate/alumina catalyst which is activated by treatment with a Group Ia metal cation salt, sodium hydroxide. The above-mentioned procedure was used except that 3.94g $H_3PO_4$ in 0.025L of solution was added to 51g of the same batch of calcined catapal alumina. Catalyst activation was effected by the titration method wherein the dried catalyst was placed in 0.1L of deionized $H_2O$ and 0.17L of 0.35M NaOH solution was added over 10 minutes to a final pH of 11.3. The solid was filtered, dried at 110° C. and was found to contain 1.43 wt% P and 1.66 wt% Na.

EXAMPLE 3

Preparation of an $AlPO_4$ Catalyst (pH=7)

This example illustrates preparation of an $AlPO_4$ catalyst. 100g $Al(NO_3)_3$ $9H_2O$ and 30.75g of 85% $H_3PO_4$ acid were mixed in 0.75L $H_2O$. 94.5g of concentrated NH4OH solution was added to 0.2L H$_2$O and the mixture added slowly to the phosphate solution until a pH of 7.0 was reached. The gel obtained was filtered, dispersed in isopropanol, refiltered and air dried. The dried solid was calcined at 650° C. for 2 hrs providing a catalyst having an Al/P ratio of 1.0 with 23.3 wt% Al and 26.9 wt% P.

Example 4

Preparation of a H$_3$PO$_4$/SiO$_2$ Catalyst

A H$_3$SiO$_2$ containing 34 wt% H$_3$PO$_4$ on silica was prepared by stray impregnation of H$_3$PO$_4$ onto granular Davison grade 59 silica gel. The catalyst was dried and collected using standard procedures.

TABLE 1

Amination of Ethanol with piperidine (PiPD)$^{(a)}$

| Example | Catalyst | Temp °C. | PiPD Conversion % | Selectivities (mol %)$^{(b)}$ | | | | | Calcination Temp °C. |
|---|---|---|---|---|---|---|---|---|---|
| | | | | NEP | REP | DREP | DEE | C$_2$ = | |
| 1 | H$_3$PO$_4$/Al$_2$O$_3$ | 358 | 70 | 83 | 1 | 2 | 12 | 2 | |
| 2 | pH = 11 | 354 | 69 | 89 | 1 | 2 | 7 | 1 | — |
| 3 | AlPO$_4$ -1.0 | 358 | 75 | 85 | 1 | 5 | 6 | 3 | 650 |
| 4 | H$_3$PO$_4$/SiO$_2$ | 355 | 76(c) | 80 | — | — | 4 | 16 | — |

$^{(a)}$P = 240 psig, PiPD/ETOH feed molar ratio = 1, GHSV = 160h$^{-1}$
$^{(b)}$NEP = N-ethylpiperidine; REP = ring substituted ethyl pipD; DREP = Di-ring ethyl pipD; DEE = diethyl ether; C$_2$ = = ethylene
(c)GHSV = 640 h$^{-1}$
(d)GHSV = CC feed (STP)/CC catalyst/hr.

Table 1 lists the performance of the above-mentioned catalysts in the reaction of ethanol with piperidine wherein the following test procedure was used. 14cc of 10–16 mesh catalyst was loaded into a 9/16″ O.D. stainless steel reactor tube. The reactor was placed in a conventional tube furnace such that the catalyst bed was centrally and uniformly heated to a constant temperature The reactor was first pressurized with the amine/alcohol mixture, except example 4 where the reactor was pressurized after heating to reaction temperature. The catalyst bed was raised to the final temperature with the feed mixture flowing at a rate such that the desired LHSV or GHSV was obtained. Product samples were collected during the run and analyzed by well established gas chromatographic techniques.

The results presented in Table 1 demonstrate that phosphorus-containing catalysts activated by treatment with a Group Ia or IIa metal cation salt provide high selectivity toward the desired N-alkylated product without sacrificing conversion. Reaction examples 1 and 2 provide a direct comparison of reaction products obtained under similar reaction conditions by employing activated versus unactivated phosphorus-containing catalysts. The base treated catalyst of example 2 provides a 6% increase in selectivity toward the N-alkylated product while providing a 40% relative decrease in diethyl ether formation with conversion remaining constant. Example 3 discloses the phosphorus-containing catalyst, AlPO$_4$ which has been precipitated with ammonium hydroxide solution to a final pH of 7.0 such that a 1:1 stoichiometric precipitate of aluminum and phosphate is formed. Preparations of aluminum phosphate having a pH less than 7.0 contain residual acidity which detrimentally effects product selectivity.

From these results it is apparent that base treated phosphorus-containing catalysts can be successfully employed in a process for the selective amination of 1° and 2° alcohols and diols. Additionally, these catalysts reduce by-product formation thereby reducing costs associated with complex separation of chemical mixtures.

Having thus described the present invention, what is now deemed appropriate for Letters Patent of the United States is set out in the following appended claims.

What is claimed is:

1. In a process for aminating alcohols and diols by contacting an amine with a 1° or 2° alcohol or diol in the presence of a phosphorus-containing catalyst having acidic surface sites, the improvement for selectively producing N-alkylated amines which comprises: activating said phosphorus-containing catalyst by base treatment with an effective amount of a Group Ia or IIa cation metal salt sufficient to render basic the acidic sites on the surface of the catalyst.

2. The process as defined in claim 1 wherein said amine is selected from the group consisting of methylamine, ethylamine, piperidine, diethylamine and aniline.

3. The process as defined in claim 1 wherein said 1° or 2° alcohol or diol is selected from the group consisting of C$_1$–C$_8$ linear and branched acyclic, cyclic and aromatic alcohols.

4. The process as defined in claim 3 wherein said 1° or 2° alcohol or diol is selected from the group consisting of methanol, ethanol, isopropanol, ethylene glycol, benzyl alcohol, butanediol and benzenedimethanol.

5. In a process for the amination of an alcohol by contacting piperidine with ethanol in the presence of a phosphorous-containing catalyst, the improvement for selectively producing N-ethylpiperidine which comprises: activating said phosphorus-containing catalyst by base treatment with an effective amount of a Group Ia or IIa cation metal salt sufficient to render basic the acidic sites on the surface of the catalyst.

6. The process as defined in claim 5 wherein said metal cation salt is an alkyl salt of a metal selected from group Ia and IIa of the Periodic Table of the elements.

7. The process as defined in claim 6 wherein said alkyl salt of a metal selected from group Ia and IIa of the Period Table of the elements is selected from the group consisting of methyl lithium and diethyl magnesium.

8. The process as defined in claim 5 wherein said phosphorus-containing catalyst is selected from the group consisting of phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, boron phosphate, aluminum phosphate, ferric phosphate, titanium phosphate, zirconium phosphate and lanthanum phosphate.

9. The process as defined in claim 5 wherein said alkali or alkaline earth metal cation salt is represented by the formula:

$$M_a{}^{m+}X_b{}^{n-}$$

wherein $M^{m+}$ is a cation selected from Group Ia and IIa of the Periodic Table of the elements having a valence m, $X^{n-}$ is an organic or inorganic anionic species having a valence n, and a and b are integers such that the ratio of a to b provides a neutral salt.

10. The process as defined in claim 9 wherein said phosphorus-containing catalyst is $H_3PO_4$ and said metal cation salt is sodium hydroxide.

11. The process as defined in claim 5 further comprising the step of dispersing said phosphorus-containing catalyst onto an inert media selected from the group consisting of alumina, silica-alumina, magnesia and diatomaceous earth prior to activating said catalyst with said alkali or alkaline earth metal cation salt.

12. The process as defined in claim 5 wherein said phosphorus-containing catalyst is activated by insipiently wetting said catalyst with an amount of metal cation salt solution equal to at least one equivalent of phosphorus in the phosphorus-containing catalyst.

13. The process as defined in claim 5 wherein said phosphorus-containing catalyst is activated by adding said catalyst to a volume of solvent sufficient to form a slurry and adding an amount of metal cation salt sufficient to adjust said slurry to a pH of between about 7 and 11.5.

14. The process as defined in claim 5 further comprising the step of calcining said activated phosphorus-containing catalyst at a temperature between 250° C. and 600° C.

15. The process as defined in claim 5 wherein said process for the amination of an alcohol is run as a vapor phase reaction at a temperature ranging from about 150° C. to about 500° C. and pressure ranging from about 1 to 100 atmospheres.

16. The process as defined in claim 5 wherein said process for the amination of an alcohol is run as a liquid phase reaction at temperatures ranging from 100° C. to about 400° C.

17. The process as defined in claim 9 wherein $X^{n-}$ is an organic or inorganic anionic species selected from the group consisting of an hydroxide, $C_1$–$C_4$ alkoxide and nitrate.

* * * * *

UNITED STATES PATENT AND TRADEMARK OFFICE
CERTIFICATE OF CORRECTION

PATENT NO. : 4,950,690

DATED : August 21, 1990

INVENTOR(S) : Parris, et al.

It is certified that error appears in the above-identified patent and that said Letters Patent is hereby corrected as shown below:

Title page: Col. 1.

In the title:

"ANIMATION" should be -- AMINATION --.

In the Specification:

Column 2, Line 55, "amInes" should be -- amines --.

Column 6, Line 26, between "synthesis" and "For" insert -- . --.

Column 7, Line 12, between "A" and "containing" delete "$H_3SiO_2$" insert -- $H_3PO_4/SiO_2$ --.

Column 7, Line 37, insert -- . -- between "temperature" and "The".

In the Claims:

Column 9, Line 19, "insipiently" should be -- incipiently --.

Signed and Sealed this

Twenty-first Day of July, 1992

Attest:

DOUGLAS B. COMER

Attesting Officer

Acting Commissioner of Patents and Trademarks